US009198364B2

(12) United States Patent
Becker

(10) Patent No.: US 9,198,364 B2
(45) Date of Patent: Dec. 1, 2015

(54) DOWNY MILDEW RESISTANCE IN TABLE BEET

(75) Inventor: Christopher Hans Becker, Mt. Vernon, WA (US)

(73) Assignee: ALF CHRISTIANSON SEED COMPANY, Burlington, WA (US)

( * ) Notice: Subject to any disclaimer, the term of this patent is extended or adjusted under 35 U.S.C. 154(b) by 950 days.

(21) Appl. No.: 13/405,025

(22) Filed: Feb. 24, 2012

(65) Prior Publication Data

US 2013/0227721 A1    Aug. 29, 2013

(51) Int. Cl.
*A01H 1/04* (2006.01)
*A01H 5/06* (2006.01)

(52) U.S. Cl.
CPC ........................................ *A01H 5/06* (2013.01)

(58) Field of Classification Search
None
See application file for complete search history.

(56) References Cited

U.S. PATENT DOCUMENTS 6,555,375 B1    4/2003  Golovko
6,956,149 B1   10/2005  Richards et al.

OTHER PUBLICATIONS

McGrath et al. (The Plant Genome (a supplement to Crop Science), Jan. 2007, No. 1, pp. s-27-s-44).*
McFarlane, J.S., Breeding for resistance to downy mildew in sugar beets, Proc. Am. Soc. Sugar Beet Technol., Feb. 1952, vol. 7, pp. 415-420.
Russell, G.E., Experiments in selecting for resistance to downy mildew in sugar beet, The Journal of Agricultural Science, Oct. 1968, vol. 71(02), pp. 251-256.
Channon, A.G., Resistance of the Red Beet Cultivar Avonearly to Infection by *Peronospora farinosa* f.sp. *betae*, Plant Pathology, Jan. 1969, vol. 18(2), pp. 89-93.
Draycott, A.P. editor, Sugar Beet, Oxford Blackwell Publishing Ltd, Oxford, UK, 2006, p. 75.
Du Toit, L.J., Crop Profile for Table Beet Seed in Washington, Washington State University, publication No. MISC0356E, Aug. 2007, 13 pages.
Harveson, R.M. et al. editors, Compendium of Beet Diseases and Pests, 2nd ed., American Phytopathological Society Press, St. Paul, MN, 2009, pp. 17-18.
Hummert International of Missouri and Kansas, Hummert Seed Catalog, USA, 2013, 1 page.
Southern Exposure Seed Exchange, Detroit Dark Red Beet, Retrieved from http://www.southernexposure.com/detroit-dark-red-beet-5-g-p-1108.html, (2014).
Territorial Seed Company, Beets: Pacemaker III Beet, Retrieved from http://www.territorialseed.com/product/554/beet_seed, (2012).
Goldman, I. editor, Revised Jun. 20, 2010, Vegetable Cultivar Descriptions:Beet,Lists 1-26 combined, Retrieved from http://cuke.hort.ncsu.edu/cucurbit/wehner/vegcult/beet.html.
McFarlane, J. S. (author), "Breeding for resistance to downy mildew in sugar beets" (title), Proc. Am. Soc. Sugar Beet Technol (publisher: American Society of Sugar Beet Technologists, place of publication: US) vol. 7, pp. 415-420, (1952).
Russell, G. E. (author), "Experiments in selecting for resistance to downy mildew in sugar beet" (title), The Journal of Agricultural Science, Cambridge, UK (publisher: Plant Breeding Institute, Trumpington, Cambridge, UK, place of pub: Cambridge U, (1968).
Channon, A.G. (author), "Resistance of the Red Beet Cultivar Avonearly to Infection by *Peronospora farinosa* f.sp. *betae*" (title), Plant Pathology (publisher: National Vegetable Research Station, Wellesbourne, Warwick, UK, place of publication: UK), (1969).
"Sugar Beet" (book title), Edited by Draycott, A.P. (author), publisher: Oxford Blackwell Publishing Ltd, 9600 Garsington Road, Oxford OX4 2DQ, UK places of publication: UK, USA, AU, (2006).
Du Toit, L.J. (author), "Crop Profile for Table Beet Seed in Washington" (title), publisher: Washington State University, publication No. MISC0356E; 13 pages submitted and relied on; publication date, Aug. 2007, place of pub: Washington State, USA, (2009).
"Compendium of Beet Diseases and Pests" (title), Edited by Harveson, R. M., Hanson, L. E. and Hein, G. L. (authors), published by: St. Paul, MN: American Phytopathological Society Press (published in the USA), (2009).
"Hummert Seed Catalog" (title), by Hummert International of Missouri and Kansas, USA, www.hummert.com (publisher and author is Hummert International and document was published in the USA), (2013).

* cited by examiner

*Primary Examiner* — David T Fox
*Assistant Examiner* — Jared Shapiro
(74) *Attorney, Agent, or Firm* — Jondle & Associates, P.C.

(57) ABSTRACT

The present invention relates to a beet plant, seed, variety and hybrid. More specifically, the invention relates to a beet plant having a mutant allele designated ACSDMR001 which confers resistance to downy mildew infection. The invention also relates to crossing inbreds, varieties and hybrids containing the ACSDMR001 allele to produce novel types and varieties of beet plants having downy mildew resistance.

23 Claims, No Drawings

DOWNY MILDEW RESISTANCE IN TABLE BEET

BACKGROUND OF THE INVENTION

The present invention relates to a novel mutant allele of *Beta vulgaris* designated ACSDMR001, which results in a high resistance to the downy mildew pathogen *Peronospora farinose* f. sp. *betae* (syn. *P. schactii*). The present invention also relates to *B. vulgaris* seed, *B. vulgaris* plants and parts thereof, and *B. vulgaris* varieties and hybrids which contain the mutant allele. In addition, the present invention is directed to transferring the ACSDMR001 mutant allele to other plants in the same genus lacking the allele, and is useful for producing novel types and varieties of downy mildew resistant *Beta vulgaris*. All publications cited in this application are herein incorporated by reference.

The beet (*Beta vulgaris*) is a plant in the Amaranthaceae family. Beet is best known for its numerous cultivated varieties, the most common one being the purple root vegetable known as beetroot or garden beet. However, other cultivated varieties in the *Beta* genus include the leaf vegetables chard and spinach beet, as well as the root vegetables sugar beet, which is important in the production of table sugar, and magelwurzel, which is a fodder crop. Three subspecies are typically recognized: *Beta vulgaris* subsp. *vulgaris*, *Beta vulgaris* subsp. *maritima*, and *Beta vulgaris* subsp. *adanensis*. All cultivated varieties fall into the subspecies *Beta vulgaris* subsp. *vulgaris*, while *Beta vulgaris* subsp. *maritima*, commonly known as the sea beet, is the wild ancestor of these and is found throughout the Mediterranean, the Atlantic coast of Europe, the Near East, and India. Another wild subspecies, *Beta vulgaris* subsp. *adanensis*, occurs from Greece to Syria.

*Beta vulgaris* is an herbaceous biennial or, rarely, perennial plant with leafy stems. Garden beets are grown for the roots, which are eaten cooked, as a vegetable, in salads or pickled. Chard and spinach beet are grown for the leaves, which are used as a potherb and in salads. The roots and leaves of the beet have also been used in folk medicine to treat a wide variety of ailments.

Downy mildew is a harmful disease of beet that can lead to economic losses in both seed and commercial production fields. Downy mildew is caused by the plant pathogen *Peronospora farinosa* f. sp. *beticola* (Pfb), which persists as oospores in the soil, on beet seed crops, or on overwintered volunteer beet plants. Attacks are most damaging at the seedling stage. The cotyledons are systemically infected, becoming discolored and distorted, and loss of seedlings causes uneven crop development. The infection is favored by wet and cool weather conditions, and may appear in early spring and recur in autumn. Under cool wet conditions, sporangia of Pfb can germinate on the leaf surface in 2-6 hours. Infection of leaf tissue is usually completed after 3-4 hours. The development of lesions is favored by temperatures of approximately 20° C. and under these ideal conditions sporulation usually occurs 6-7 days after infection but it can be up to 12 days. Control relies on adequate crop rotations, and avoidance of sources of infection. Beet varieties that exhibit a high level of resistance to downy mildew infection are highly desirable.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include increased fruit size and weight, higher seed yield, improved color, resistance to diseases and insects, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, the overall value of the advanced breeding lines, and the number of successful cultivars produced per unit of input (e.g., per year, per dollar expended, etc.).

Promising advanced breeding lines are thoroughly tested and compared to appropriate standards in environments representative of the commercial target area(s) for at least three years. The best lines are candidates for new commercial cultivars. Those still deficient in a few traits are used as parents to produce new populations for further selection.

These processes, which lead to the final step of marketing and distribution, usually take from many years from the time the first cross or selection is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of beet plant breeding is to develop new, unique, and superior beet cultivars. The breeder initially selects and crosses two or more parental lines, followed by repeated selfing and selection, producing many new genetic combinations. The breeder can theoretically generate billions of different genetic combinations via crossing, selfing, and mutations. The breeder has no direct control at the cellular level. Therefore, two breeders will never develop the same line, or even very similar lines, having the same beet traits.

Each year, the plant breeder selects the germplasm to advance to the next generation. This germplasm is grown under different geographical, climatic, and soil conditions, and further selections are then made during, and at the end of, the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop superior beet cultivars.

Descriptions of breeding methods that are commonly used for different traits and crops can be found in one of several reference books (e.g., *Principles of Plant Breeding*, John Wiley and Son, pp. 115-161 (1960); Allard (1960); Simmonds (1979); Sneep, et al. (1979); Fehr (1987); "Carrots and Related Vegetable *Umbelliferae*," Rubatzky, V. E., et al. (1999).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs, as well as technical superiority of the final cultivar. For seed-propagated cultivars, it must be feasible to produce seed easily and economically.

Beet is an important and valuable vegetable crop. Thus, a continuing goal of beet plant breeders is to develop stable, high yielding beet cultivars that are agronomically sound. To accomplish this goal, the beet breeder must select and develop beet plants with traits that result in superior cultivars. The development of beet varieties having an increased level of resistance to downy mildew is very important for improving beet production.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments are described in conjunction with systems, tools, and methods which are meant to be exemplary and illustrative, not limiting in scope. In various embodiments, one or more of the above-described problems have been reduced or eliminated, while other embodiments are directed to other improvements.

According to the invention, there is provided a novel mutant allele derived from *Beta vulgaris* designated ACSDMR001. This invention thus relates to *B. vulgaris* seed, *B. vulgaris* plants, and *B. vulgaris* varieties and hybrids, and to methods for producing *B. vulgaris* plants. More specifically, the invention relates to a mutant allele designated ACSDMR001, which produces a *B. vulgaris* plant with a high downy mildew resistance.

Another embodiment of the invention relates to any *B. vulgaris* seed, plant, or part thereof, having mutant allele ACSDMR001.

The invention also provides methods for introducing the mutant allele of the present invention into plants by crossing a plant which lacks the mutant allele with a plant that has allele ACSDMR001, selfing the resulting generations and then selecting for plants exhibiting high downy mildew resistance.

In another embodiment, the invention provides a method for producing a hybrid beet seed comprising crossing a first plant parent with a second plant parent and harvesting the resultant hybrid beet seed, wherein either one or both parents contain allele ACSDMR001. The hybrid seeds, plant and parts thereof produced by such method are also part of the invention.

In another embodiment, the invention provides a method for producing a hybrid beet-chard plant comprising crossing a beet plant with a chard plant and harvesting the resultant hybrid beet-chard seed, wherein one or both parents contain mutant allele ACSDMR001. The hybrid plant and parts thereof produced by such method are also part of the invention.

Another embodiment of the invention relates to any beet-chard hybrid seed or plant having mutant allele ACSDMR001.

In another embodiment, the present invention provides regenerable cells for use in tissue culture. The tissue culture will preferably be capable of regenerating plants having essentially all of the physiological and morphological characteristics of the foregoing beet or beet-chard hybrid plant, and of regenerating plants having substantially the same genotype as the foregoing starting plant. Preferably, the regenerable cells in such tissue cultures will be callus, protoplasts, meristematic cells, cotyledons, hypocotyl, leaves, pollen, embryos, roots, root tips, anthers, pistils, shoots, stems, petiole, flowers, and seeds. Still further, the present invention provides beet plants regenerated from the tissue cultures of the invention.

Another embodiment of the invention is to provide methods for producing other beet plants containing the mutant allele ACSDMR001. Beet cultivars derived by the use of those methods are also part of the invention.

The present invention also relates to methods for producing a beet plant containing in its genetic material one or more transgenes and to the transgenic beet plant produced by those methods.

In another embodiment, the present invention provides for single gene converted plants. The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring beet gene or a transgene introduced through genetic engineering techniques.

The invention further provides methods for developing beet plants and beet-chard hybrid plants in a beet plant breeding program using plant breeding techniques including recurrent selection, backcrossing, pedigree breeding, restriction fragment length polymorphism enhanced selection, genetic marker enhanced selection, and transformation. Seeds, beet plants, and parts thereof, produced by such breeding methods are also part of the invention.

The invention further provides for a beet plant having a high resistance level to downy mildew and exhibiting a decreased or lower average number of downy mildew sporangia per grams of leaf tissue when compared to commercial beet varieties grown in an environment where downy mildew is present. A high resistance level exhibits at least between 75% and 25%, including 75%, 73%, 72%, 65%, 60%, 59%, 58%, 55%, 53%, 50%, 47%, 45%, 42%, 38%, 33%, 31%, 29%, 28%, 27%, and 25%, or any integer or fraction thereof, lower average number of downy mildew sporangia per grams of leaf tissue per plant. In certain environments, the plant of the present invention, which contains mutant allele ACS-DMR001, exhibits greater than 75% less average number of downy mildew sporangia per grams of leaf tissue versus commercial beet varieties. In certain environments, the plant of the present invention, which contains mutant allele ACS-DMR001, exhibits zero number of downy mildew sporangia per grams of leaf tissue.

In addition to the exemplary embodiments described above, further aspects and embodiments will become apparent by study of the following descriptions.

DETAILED DESCRIPTION OF THE INVENTION

In the description and tables which follow, a number of terms are used. In order to provide a clear and consistent understanding of the specification and claims, including the scope to be given such terms, the following definitions are provided:

ACSDMR001. Refers to the mutant allele of the present invention which confers a high resistance level to downy mildew to beet plants. A representative sample of said mutant allele has been deposited under ATCC Accession Number PTA-12501.

Allele. The allele is any of one or more alternative forms of a gene, all of which relate to one trait or characteristic. In a diploid cell or organism, the two alleles of a given gene occupy corresponding loci on a pair of homologous chromosomes.

Alter. The utilization of up-regulation, down-regulation, or gene silencing.

Backcrossing. Backcrossing is a process in which a breeder repeatedly crosses hybrid progeny back to one of the parents, for example, a first generation hybrid $F_1$ with one of the parental genotype of the $F_1$ hybrid.

Beet. Beet is a plant in the Amaranthaceae family best known for the production of a purple root vegetable, beetroot or garden beet, and also includes chard, spinach beet, sugar beet and mangelwurzel.

*Beta vulgaris*. Refers to a beet plant. Beet is a plant in the Amaranthaceae family best known for the production of a purple root vegetable, beetroot or garden beet. *Beta vulgaris* includes the subspecies chard, spinach beet, sugar beet, and mangelwurzel.

Cell. As used herein, "cell" includes a plant cell, whether isolated, in tissue culture, or incorporated in a plant or plant part.

Chard. Chard is a variety of beet, *Beta vulgaris* subsp. *cicla*, which has been bred for leaves instead of roots and is used as a leaf vegetable. It is also known as Swiss chard.

Commercial beet. Refers to a beet (*B. vulgaris*) that has been commercially sold.

Downy mildew. A disease caused by the plant pathogen *Peronospora farinosa*, characterized by gray, velvety patches of spores on the lower surfaces of leaves and often resulting in foliage blights, distortion and reduced yield.

Downy mildew sporangia. The asexual spores of *Peronospora farinose* f. sp. *beticola* (Pfb).

Essentially all the physiological and morphological characteristics. A plant having essentially all the physiological and morphological characteristics means a plant having the physiological and morphological characteristics of the recurrent parent, except for the characteristics derived from the converted gene.

Gene. As used herein, "gene" refers to a segment of nucleic acid. A gene can be introduced into a genome of a species, whether from a different species or from the same species, using transformation or various breeding methods.

Genotype. Refers to the genetic constitution of a cell or organism.

High resistance level. Refers to a beet plants' level of resistance to downy mildew in which the plant exhibits a decreased or lower average number of downy mildew sporangia per grams of leaf tissue when compared to commercial beet varieties grown in an environment where downy mildew is present. A high resistance level exhibits at least between 75% and 25%, including 75%, 73%, 72%, 65%, 60%, 59%, 58%, 55%, 53%, 50%, 47%, 45%, 42%, 38%, 33%, 31%, 29%, 28%, 27%, and 25%, or any integer or fraction thereof, lower average number of downy mildew sporangia per grams of leaf tissue per plant. In certain environments, the plant of the present invention, which contains mutant allele ACS-DMR001, exhibits greater than 75% less average number of downy mildew sporangia per grams of leaf tissue versus commercial beet varieties. In certain environments, the plant of the present invention, which contains mutant allele ACS-DMR001, exhibits zero number of downy mildew sporangia per grams of leaf tissue.

Homologous recombination. The physical exchange of DNA between two homologous DNA molecules.

Linkage. "Linkage" refers to a phenomenon wherein alleles on the same chromosome tend to segregate together more often than expected by chance if their transmission was independent.

Linkage disequilibrium. "Linkage disequilibrium" refers to a phenomenon wherein alleles tend to remain together in linkage groups when segregating from parents to offspring, with a greater frequency than expected from their individual frequencies.

Locus. A defined segment of DNA.

Maturity date. Maturity refers to the stage when the plants are of full size or optimum weight, in marketable form or shape to be of commercial or economic value.

Percent identity. Percent identity as used herein with respect to a comparison of two plant varieties refers to the comparison of the homozygous alleles of two plant varieties. Percent identity is determined by comparing a statistically significant number of the homozygous alleles of two developed varieties. For example, a percent identity of 90% between plant variety 1 and plant variety 2 means that the two varieties have the same allele at 90% of their loci. Percent identity as used herein with respect to two nucleic acids refers to the comparison of the entire sequence for each of the two nucleic acids and is determined by GAP alignment using default parameters (GCG, GAP version 10, Accelrys, San Diego, Calif.). GAP uses the algorithm of Needleman and Wunsch, *J Mol Biol*, 48:443-453 (1970), to find the alignment of two complete sequences that maximizes the number of matches and minimizes the number of sequence gaps. Sequences which have 100% identity are identical. The present invention encompasses nucleic acids that have about 70%, 75%, 80%, 85%, 90%, 91%, 92%, 93%, 94%, 95%, 96%, 97%, 98%, 99%, or 100% sequence identity to the specified nucleic acid.

Percent similarity. Percent similarity as used herein refers to the comparison of the homozygous alleles of one plant variety with those of another plant, and if the homozygous allele of the first plant matches at least one of the alleles from the other plant then they are scored as similar. Percent similarity is determined by comparing a statistically significant number of loci and recording the number of loci with similar alleles as a percentage. A percent similarity of 90% between the first plant and a second plant means that the first matches at least one of the alleles of the second plant at 90% of the loci.

*Peronospora farinosa* f. sp. *beticola* (Pfb). A plant pathogen that is the causative agent of downy mildew.

Plant. As used herein, the term "plant" includes reference to an immature or mature whole plant, including a plant from which seed, grain, anthers, or pistils have been removed. A seed or embryo that will produce the plant is also considered to be the plant.

Plant parts. As used herein, the term "plant parts" (or a sugar beet or root crop plant, or a part thereof) includes protoplasts, leaves, stems, roots, root tips, anthers, seed, embryo, pollen, ovules, cotyledon, hypocotyl, flower, shoot, tissue, petiole, cells, meristematic cells, and the like.

Quantitative Trait Loci. Quantitative Trait Loci (QTL) refers to genetic loci that control to some degree, numerically representable traits that are usually continuously distributed.

Regeneration. Regeneration refers to the development of a plant from tissue culture.

RHS. RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Root crop. As used herein, the term "root crop" means a plant that is cultivated primarily for its roots such as, but not limited to, cassava, taro, beets, turnips, carrots, potatoes, yams, rutabagas, radishes, jicama, or parsnips.

Root vasculature. Tissues in the plant root that are responsible for carrying nutrients to and from the root. These tissues are generally tubular.

Single gene converted. Single gene converted or conversion plant refers to plants which are developed by a plant breeding technique called backcrossing or via genetic engineering wherein essentially all of the desired morphological and physiological characteristics of a line are recovered in addition to the single gene transferred into the line via the backcrossing technique or via genetic engineering.

Sporangia. Refers to the asexual spores of *Peronospora farinose* f. sp. *beticola* (Pfb), which is the causative agent of downy mildew.

Spore. A small, usually single-celled reproductive body that is highly resistant to desiccation and heat and is capable of growing into a new organism, produced especially by certain bacteria, fungi, algae, and nonflowering plants.

Sporulation. The act or process of forming spores.

Storage tissues. In the sugar beet or root crop root, there are specific tissues for the storage of sugar. These tissues are physically and visually distinct from the root vasculature.

Taproot. A very large root used for storing plant nutrients. Sugar beets, carrots, red beets, radishes, and parsnips are all examples of plants having taproots.

Transgene. A gene that is transferred from an organism of one species to an organism of another species by genetic engineering.

The present invention relates to a new allele designated ACSDMR001 in the genus *Beta* that is phenotypically expressed as a high resistance level to downy mildew infection. As used herein, downy mildew resistance refers to plants that display highly reduced disease symptoms throughout the growing season.

According to the invention, there is provided a novel mutant allele derived from *Beta vulgaris* designated ACSDMR001. This invention thus relates to *B. vulgaris* seed, *B. vulgaris* plants, *B. vulgaris* varieties and hybrids, and to methods for producing *B. vulgaris* plants. More specifically, the invention relates to a mutant allele designated ACSDMR001, which produces a *B. vulgaris* plant with a high resistance level to downy mildew infection.

Another embodiment of the invention relates to any *B. vulgaris* seed, plant, or part thereof, having mutant allele ACSDMR001.

Another embodiment of the invention is to provide methods for producing other *B. vulgaris* plants derived from a *B. vulgaris* plant having ACSDMR001 mutant allele. *B. vulgaris* lines derived by the use of those methods are also part of the invention.

The mutant allele of the present invention is readily transferred between the deposited cultivar and its related cultivars.

A plant of the present invention can be obtained by crossing a plant containing the claimed mutant allele with any beet cultivar lacking the allele. The plant containing the allele can be any beet variety including a cultivar in which the factor has been previously genetically fixed.

Other breeding schemes can be used to introduce mutant allele ACSDMR001 into the desired cultivar. The particular scheme used is not critical to the invention, so long as the allele is stably incorporated into the genome of the cultivar. For example, a marker gene can be used. A nucleic acid probe which hybridizes to the marker gene can be used to identify the desired plants in the $F_1$ generation.

The mutant allele ACSDMR001 will advantageously be introduced into varieties that contain desirable genetic traits such as resistance to disease, drought tolerance, heat and/or cold tolerance, and the like.

The genetic factor of the present invention which is capable of transmitting downy mildew resistance, has been determined to be an allele that has been designated ACSDMR001. Based on the data presented in Tables 4 and 5, ACSDMR001 appears to be a single dominant or partially dominant mutant allele. Alternatively, the mutant allele may be governed by a dominant gene with additional modifier genes influencing the level of resistance. It is a feature of the present invention that this mutant allele ACSDMR001 may be used in and transferred among the various beet, sugar beet, and chard in the *B. vulgaris* species.

In another embodiment, the present invention provides regenerable cells for use in tissue culture. The tissue culture will preferably be capable of regenerating plants having the physiological and morphological characteristics of the foregoing *B. vulgaris* plant, and of regenerating plants having substantially the same genotype as the foregoing *B. vulgaris* plant. Preferably, the regenerable cells in such tissue cultures will be embryos, protoplasts, meristematic cells, callus, pollen, leaves, anthers, pistils, stems, petioles, roots, root tips, fruits, seeds, flowers, cotyledons, hypocotyls or the like. Still further, the present invention provides *B. vulgaris* plants regenerated from the tissue cultures of the invention.

The invention also relates to methods for producing a *B. vulgaris* plant containing in its genetic material one or more transgenes and to the transgenic *B. vulgaris* plant produced by that method.

In another embodiment, the present invention provides for single gene converted plants of ACSDMR001. The single transferred gene may preferable be a dominant or recessive allele. Preferably, the single transferred gene will confer such trait as male sterility, herbicide resistance, insect resistance, resistance for bacterial, fungal, or viral disease, male fertility, improved harvest characteristics, enhanced nutritional quality, and improved processing characteristics. The single gene may be a naturally occurring *B. vulgaris* gene or a transgene introduced through genetic engineering techniques.

The invention further provides methods for developing *B. vulgaris* plants in a *B. vulgaris* plant breeding program using plant breeding techniques including recurrent selection, backcrossing, pedigree breeding, restriction fragment length polymorphism enhanced selection, genetic marker enhanced selection and transformation. *B. vulgaris* seeds, plants and parts thereof produced by such breeding methods are also part of the invention.

The present invention is directed to developing unique plants of the *Beta* species. The beet fruit and plants of the present invention unexpectedly express a substantial increase in resistance to downy mildew. The allele of the instant invention has also been expressed in different genetic backgrounds of beet. To date, no commercialized *B. vulgaris* variety has the high resistance level to powdery mildew conferred by mutant allele ACSDMR001 of the present invention. The crosses with mutant allele ACSDMR001 of the present invention unexpectedly expressed a unique resistance pattern, in which the plants showed a consistent high resistance level throughout the whole growing season and without the aid of any chemical application. The mutant allele of the present invention allows new varieties of *B. vulgaris* to be developed that have a better and more consistent resistance to downy mildew for growers, the commercial market, and especially for organic growers.

As used herein, the term plant includes plant cells, plant protoplasts, plant cell tissue cultures from which *B. vulgaris* plants can be regenerated, plant calli, plant clumps and plant cells that are intact in plants, or parts of plants, such as embryos, pollen, ovules, flowers, stems, leaves, roots, root tips, anthers, pistils, and the like.

EXAMPLES

The following examples are provided to further illustrate the present invention and are not intended to limit the invention beyond the limitations set forth in the appended claims.

Example 1

Development of ACSDMR001, the Mutant Allele of the Present Invention

The mutant allele of the present invention, ACSDMR001, unexpectedly arose as a spontaneous mutation in a population of beet roots. A beet population derived from the cross between table beet W357B and sugar beet C6869 was obtained at a breeding nursery as part of the USDA sugar beet program in 2005. After further research, roots from this population were placed into vernalization and seed was produced, which was then sown in a field and selected for dark red petiole color. Roots from this selection were harvested and vernalized and seed was produced in a greenhouse. The line, designated AZ395, was screened for downy mildew infection and unexpectedly showed a score of 8.85 on a scale of 1 to 9, with 9 being resistance. This was followed by another round of selection for petiole color, vernalization, seed production and downy mildew tests. Of the 562 plants screened, surprisingly all came back as 100% resistant to downy mildew. Prior to the present invention, a downy mildew resistant mutation of this type in beet was unknown. Five hybrid beet lines were created using inbred AZ395 as the male parent and designated AY08525, AY08526, AY08527, AY08528, and AY08529. These lines were screened for downy mildew and all five showed 100% resistance. An additional nine hybrid beet lines were produced from crosses with inbred AZ395 and designated AY10255, AY10261, AY10267, AY10273, AY10279, AY10285, AY10291, AY10297, and AY10303. Hybrid lines AY08529, AY08525 and AY10261 were selected and assigned the codes BEH140, BEH143, and BEH150, respectively.

Example 2

Determination of Inheritance of Mutant Allele ACSDMR001

A method to determine the inheritance of mutant allele ACSDMR001 is to first obtain the ploidy of the allele in downy mildew resistant plants. Ploidy is determined by the use of flow cytometry. After ploidy is determined, crossing beet plants of the present invention with beet plants lacking mutant allele ACSDMR001 allows for determination of segregation and further defines inheritance of mutant allele ACSDMR001. Most beet types are diploid with 18 chromosomes in each cell, although some tetraploid sugar beet cultivar lines are used to breed triploid varieties by crosses with diploids. Alternatively, inheritance is determined by crossing a beet plant containing mutant allele ACSDMR001 with beet plants lacking ACSDMR001 and testing progeny for downy mildew resistance.

Example 3

Transfer of Mutant Allele ACSDMR001 to Different *Beta* Genetic Backgrounds Through Breeding The mutant allele of the present invention was transferred to other *Beta* genetic backgrounds through crossing a *Beta* line lacking mutant allele ACSDMR001 with a downy mildew resistant line carrying the mutant allele ACSDMR001. $F_1$ plants were screened for resistance to downy mildew infection. At least 14 hybrid beets containing the mutant allele ACSDMR001 were created using inbred beet AZ395 as the male parent.

Example 4

Transfer of Mutant Allele ACSDMR001 into Beet Line AC136

A hybrid beet was produced in the field in the summer of 2008 from a cross between inbred beet line AZ395, which contains mutant allele ACSDMR001, and beet line AC136, which does not contain ACSDMR001. Parental line AC136 generally displays approximately 45% resistance to downy mildew. The hybrid beet produced from the cross was designated line AY08529. Line AY08529 was screened for downy mildew in 2008 and had 100% resistance. The line was assigned the code BEH140.

Example 5

Transfer of Mutant Allele ACSDMR001 into Beet Line AC193

A hybrid beet was produced in the field in the summer of 2008 from a cross between inbred beet line AZ395, which contains mutant allele ACSDMR001, and beet line AC193, which does not contain ACSDMR001. Parental line AC193 generally displays approximately 35% resistance to downy mildew. The hybrid beet produced from the cross was designated line AY08525. Line AY08525 was screened for downy mildew in 2008 and had 100% resistance. The line was assigned the code BEH143.

Example 6

Transfer of Mutant Allele ACSDMR001 into Beet Line AC214

A hybrid beet was produced in spring of 2010 from a cross between inbred beet line AZ395, which contains the ACSDMR001 mutant allele and beet line AC214, which does not contain ACSDMR001. The hybrid beet produced from the cross was designated line AY10261. Line AY10261 was screened for downy mildew and had 91% resistance. Line AY10261 was assigned the code BEH150.

Example 7

Transfer of Mutant Allele ACSDMR001 into Beet Line AC184

A hybrid beet was produced in the field in the summer of 2008 from a cross between inbred beet line AZ395, which contains mutant allele ACSDMR001, and beet line AC184, which does not contain ACSDMR001. The hybrid beet produced from the cross was designated line AY08526. Line AY08526 was screened for downy mildew in 2008 and had 100% resistance.

Example 8

Transfer of Mutant Allele ACSDMR001 into Beet Line AC157

A hybrid beet was produced in the field in the summer of 2008 from a cross between inbred beet line AZ395, which contains mutant allele ACSDMR001, and beet line AC157, which does not contain ACSDMR001. The hybrid beet produced from the cross was designated line AY08527. Line AY08527 was screened for downy mildew in 2008 and had 100% resistance.

Example 9

Transfer of Mutant Allele ACSDMR001 into Beet Line AC123

A hybrid beet was produced in the field in the summer of 2008 from a cross between inbred beet line AZ395, which contains mutant allele ACSDMR001, and beet line AC123, which does not contain ACSDMR001. The hybrid beet produced from the cross was designated line AY08528. Line AY08528 was screened for downy mildew in 2008 and showed 100% resistance.

Example 10

Transfer of Mutant Allele ACSDMR001 into Beet Line AC236

A hybrid beet was produced in spring of 2010 from a cross between inbred beet line AZ395, which contains mutant allele ACSDMR001, and beet line AC236, which does not contain ACSDMR001. The hybrid beet produced from the cross was designated line AY10255. Line AY10255 was screened for downy mildew and had 88% resistance.

Example 11

Transfer of Mutant Allele ACSDMR001 into Beet Line AC258

A hybrid beet was produced in spring of 2010 from a cross between inbred beet line AZ395, which contains mutant allele ACSDMR001, and beet line AC258, which does not contain ACSDMR001. The hybrid beet produced from the cross was designated line AY10267. Line AY10267 was screened for downy mildew and had 92% resistance.

Example 12

Transfer of Mutant Allele ACSDMR001 into Beet Line AC274

A hybrid beet was produced in spring of 2010 from a cross between inbred beet line AZ395, which contains mutant allele ACSDMR001, and beet line AC274, which does not contain ACSDMR001. The hybrid beet produced from the cross was designated line AY10273. Line AY10273 was screened for downy mildew and had 99% resistance.

Example 13

Transfer of Mutant Allele ACSDMR001 into Beet Line AC290

A hybrid beet was produced in spring of 2010 from a cross between inbred beet line AZ395, which contains mutant allele ACSDMR001, and beet line AC290, which does not contain ACSDMR001. The hybrid beet produced from the cross was designated line AY10279. Line AY10279 was screened for downy mildew and had 97% resistance.

Example 14

Transfer of Mutant Allele ACSDMR001 into Beet Line AC305

A hybrid beet was produced in spring of 2010 from a cross between inbred beet line AZ395, which contains mutant allele ACSDMR001, and beet line AC305, which does not contain ACSDMR001. The hybrid beet produced from the cross was designated line AY10285. Line AY10285 was screened for downy mildew and had 92% resistance.

Example 15

Transfer of Mutant Allele ACSDMR001 into Beet Line AC311

A hybrid beet was produced in spring of 2010 from a cross between inbred beet line AZ395, which contains mutant allele ACSDMR001, and beet line AC311, which does not contain ACSDMR001. The hybrid beet produced from the cross was designated line AY10291. Line AY10291 was screened for downy mildew and had 39% resistance.

Example 16

Transfer of Mutant Allele ACSDMR001 into Beet Line AC325

A hybrid beet was produced in spring of 2010 from a cross between inbred beet line AZ395, which contains mutant allele ACSDMR001, and beet line AC325, which does not contain ACSDMR001. The hybrid beet produced from the cross was designated line AY10297. Line AY10297 was screened for downy mildew and had 86% resistance.

Example 17

Transfer of Mutant Allele ACSDMR001 into Beet Line AC332

A hybrid beet was produced in spring of 2010 from a cross between inbred beet line AZ395, which contains mutant allele ACSDMR001, and beet line AC332, which does not contain ACSDMR001. The hybrid beet produced from the cross was designated line AY10303. Line AY10303 was screened for downy mildew and had 80% resistance.

Example 18

Morphological Descriptions

Table 1 shows morphologic traits and characteristics of inbred beet line AZ395 and hybrid beets BEH140 and BEH143, which contain the mutant allele of the present invention, compared to the closest commercial beet variety, Red Ace, and the closest chard variety, Gazelle (based primarily on data collected in Salinas, Calif. in December of 2011, approximately 4 months from sowing).

TABLE 1

| Characteristic | AZ395 | BEH140 | BEH143 | Red Ace | Gazelle |
|---|---|---|---|---|---|
| Kind | Garden beet for baby leaf production | Garden beet for baby leaf production | Garden beet for baby leaf production | Garden beet or baby leaf production | Chard |
| Type | Leaf beet | Leaf beet | Leaf beet | High tonnage yield | Leaf chard |
| Chromosome ploidy | Diploid | Diploid | Diploid | Diploid | Diploid |
| Seed | Multigerm | Multigerm | Multigerm | Multigerm | Multigerm |
| Region of best adaptation | Most beet growing regions, especially U.S. and Europe | Most beet growing regions, especially U.S. and Europe | Most beet growing regions, especially U.S. and Europe | Most beet growing regions, especially U.S. and Europe | Most chard growing regions, especially U.S. and Europe |
| Maturity date | 45 days | 45 days | 45 days | 55 days | 55 days |
| Leaf number | Numerous (≥15) | Numerous (≥15) | Numerous (≥15) | Numerous (≥15) | Numerous (≥15) |
| Leaf dimension | Longer than broad | Longer than broad | Longer than broad | Longer than broad | Longer than broad |
| Leaf texture | Smooth | Smooth | Smooth | Smooth | Smooth |
| Leaf carriage | Erect | Semi-erect | Semi-erect | Erect | Semi-erect |
| Leaf apex | Rounded | Rounded | Rounded | Pointed | Rounded |
| Leaf surface | Glossy | Dull | Dull | Glossy | Glossy |
| Leaf margin | Curled, incised | Curled, incised | Curled, incised | Curled, incised | Curled, incised |
| Leaf color (upper surface) | RHS 137A (Green) | RHS 147A (Yellow-green) | RHS 147A (Yellow-green) | RHS 146A (Yellow-green) | RHS 147A (Yellow-green) |
| Leaf color (lower surface) | RHS 137B (Green) | RHS 147A (Yellow-green) | RHS 147B (Yellow-green) | RHS 146A (Yellow-green) | RHS 137A (Green) |
| Vein color (upper surface) | RHS 59C (Red-purple) | RHS 60C (Red-purple) | RHS 60A (Red-purple) | RHS 59A (Red-purple) | RHS 187B (Greyed-purple) |
| Vein color (lower surface) | RHS 59C (Red-purple) | RHS 60C (Red-purple) | RHS 60A (Red-purple) | RHS 59A (Red-purple) | RHS 187B (Greyed-purple) |
| Leaf color change | Does not redden | Does not redden | Does not redden | Does not redden | Does not redden |
| Leaf length (cm) | 24.0 | 23.0 | 24.0 | 22.0 | 28.0 |
| Leaf width (cm) | 14.0 | 12.0 | 14.0 | 13.0 | 15.0 |
| Petiole color | RHS 60C (Red-purple) | RHS 60B (Red-purple) | RHS 60B (Red-purple) | RHS 59A (Red-purple) | RHS 187C (Greyed-purple) |
| Petiole length (cm) | 30.0 | 38.0 | 35.0 | 25.0 | 32.0 |
| Petiole width (cm) | 1.5 | 1.5 | 1.0 | 1.0 | 2.5 |
| Petiole shape | Twisted | Not twisted | Not twisted | Twisted | Twisted |
| Root type | Not fleshy | Not fleshy | Not fleshy | Not fleshy | Not fleshy |
| Root crown diameter (mm) | 45.0 | 60.0 | 60.0 | 80.0 | 60.0 |
| Root shoulder shape | Sloping | Rounded | Rounded | Rounded | Sloping |
| Root shape | Cylindrical | Cylindrical | Cylindrical | Spherical | Cylindrical |
| Root surface color (above ground) | Yellow | Red | Red | Yellow | Yellow |
| Root surface color (below ground) | Red | Brownish-red | Brownish-red | Red | Red |
| Root surface texture | Roughened | Roughened | Roughened | Roughened | Roughened |
| Root flesh color | Light red | Dark red | Dark red | Dark red | Dark red |
| Root cross section zones | Distinct | Distinct | Distinct | Distinct | Distinct |

TABLE 1-continued

| Characteristic | AZ395 | BEH140 | BEH143 | Red Ace | Gazelle |
|---|---|---|---|---|---|
| Root length (mm) | 140.0 | 180.0 | 160.0 | 100.0 | 120.0 |
| Root diameter (mm) | 40.0 | 70.0 | 80.0 | 90.0 | 70.0 |
| Tap root type | Coarse | Coarse | Coarse | Coarse | Coarse |
| Root exposure above ground | None | 25% | 25% | 25% | 25% |
| Root color | RHS 186A (Greyed-purple) | RHS 59A (Red-purple) | RHS 59A (Red-purple) | RHS 186A (Greyed-purple) | RHS 186B (Greyed-purple) |

Example 19

Inoculation Procedures for Downy Mildew

An isolate of *Peronospora farinosa* f. sp. *beticola* (Pfb) was maintained on live plants of a susceptible Swiss chard variety. Sporulating cotyledons were harvested from an entire flat and put in a plastic bag with 200 mL of water and agitated for two minutes to produce a spore suspension. The spore suspension was poured through four layers of cheesecloth to remove debris. The spore suspension was quantified using a hemocytometer.

Seedlings were inoculated with a spore concentration of $2.0\times10^5$ sporangia per milliter (sp/mL) using an airbrush sprayer until runoff. Immediately after inoculation, the plants were placed into a dew chamber at 18° C. and 100% humidity for 24 hours. At the end of 24 hours, the plants were moved to a growth chamber set at 20° C. with a day length of 9 hours.

Approximately 6 days after inoculation, the seedlings were placed back into a dew chamber at 18° C. and 100% humidity for 24 hours to induce sporulation. Seedlings were harvested from a complete flat, put into a plastic bag, and weighed. After weighing, 50.0 mL of water was added to each bag and the suspension was agitated for 2 minutes. The spore suspension was then poured through four layers of cheesecloth to remove debris and the spores were quantified using a hemocytometer.

Example 20

Evaluation of Inbred Beet AZ395 for Downy Mildew

As shown in Table 2, the advanced breeding line of *Beta vulgaris* subsp. *vulgaris* AZ395, which contains the mutant allele of the present invention, was evaluated for its quantifiable resistance to Pfb infection. Entries were coded before planting and evaluation to reduce any bias in the test; entry names were not given until testing was completed. Entries C869 and W357B were used as parents for the original cross of line AZ395, and entry A97601 was included as a Pfb susceptible check.

The four entries were sown into P1040 plastic flats using soilless media and covered with medium coarse vermiculite. One entry was sown per flat with 10 rows per entry and 20 seeds per row. Plants were germinated at 21-23° C. under 9 hours of light for a period of nine days before inoculation. Plants were fertilized as needed with a liquid fertilizer and inoculated with Pfb, as described.

Four separate counts were taken per entry using a hemocytometer and counting the number of spores (or sporangia) on a 1 mm square grid on a compound microscope at 125× magnification. The average of four counts was used to calculate the concentration of sporangia per milliter (sp/mL). The total spore concentration was calculated by multiplying the average number of sporangia counted per mL by the total volume (mL) of water. The spore concentration was then divided by the weight (g) of leaf tissue harvested for each corresponding entry to calculate the total number of sporangia per gram of leaf tissue (sp/g). Table 2 shows the beet variety in column 1, the leaf tissue weight (g) in column 2, the water added (mL) in column 3, the sporangia recovered (sp/mL) in column 4, the sporangia concentration (sp) in column 5, and the sporangia per leaf tissue (sp/g) in column 6.

TABLE 2

| Entry | Leaf tissue (g) | Water (mL) | Sporangia (sp/mL) | Concentration (sp) | Sporangia/ Leaf tissue (sp/g) |
|---|---|---|---|---|---|
| AZ395 | 37.52 | 50.0 | 0 | 0 | 0 |
| C869 | 42.70 | 50.0 | 17,500 | 875,000 | 20,492 |
| W357B | 22.50 | 50.0 | 453,000 | 22,650,000 | 1,006,667 |
| A97601 | 37.78 | 50.0 | 291,500 | 14,575,000 | 419,063 |

As shown in Table 2, all entries evaluated, including the parental lines of AZ395, C869 and W357B, showed both signs and symptoms of infection by Pfb, with the exception of AZ395, which contains the mutant allele of the present invention. Infected leaves were chlorotic and malformed with sporangiophores and sporangia evident with the naked eye. Leaves of AZ395 showed no signs of infection and no sporangia were visible.

Example 21

Comparison of Inbred Beet AZ395 Versus Commercial Varieties

As shown in Table 3, the advanced breeding line of *Beta vulgaris* subsp. *vulgaris* AZ395, which contains the mutant allele of the present invention, was evaluated for its quantifiable resistance to Pfb infection and compared to the commercial beet varieties Red Ace, Kestrel, Detroit Short Top, Detroit Supreme, and Ruby Queen, as well as the chard variety Gazelle, a rhubarb variety and the Pfb susceptible check A97601. Evaluation consisted of inoculating seedlings with 8,000 spores/mL and then harvesting all plants in the flat into a plastic bag. All of the seedlings from the flat were weighed prior to adding 250 mL water. Seedlings were shaken for 1 minute in a 0.5 gallon plastic bag with the 250 mL of water. After shaking vigorously, liquid was poured through 4 layers of cheese cloth into a flask. Approximately one drop was dispensed on the counting chamber, and spores were counted under a compound microscope and the number recorded in spores/mL of liquid. Table 3 shows the variety name in column 1, plant weight (g) in column 2, water added (mL) in column 3, sporangia concentration (sp/mL) in column 4, and the sporangia per leaf tissue (sp/g) in column 5.

TABLE 3

| Variety | Plant weight (g) | Water (mL) | Sporangia (sp/mL) | Sporangia/ Leaf tissue (sp/g) |
| --- | --- | --- | --- | --- |
| AZ395 | 92.9 | 250 | 0 | 0 |
| A97601 | 45.3 | 250 | 10,000 | 55,188 |
| Gazelle | 97.54 | 250 | 2,000 | 5,126 |
| Red Ace | 71.51 | 250 | 10,000 | 34,960 |
| Kestrel | 67.85 | 250 | 8,000 | 29,477 |
| Detroit Short Top | 34.43 | 250 | 6,000 | 43,567 |
| Detroit Supreme | 101.89 | 250 | 10,000 | 24,536 |
| Ruby Queen | 117.7 | 250 | 10,000 | 21,240 |
| Rhubarb | 118.37 | 250 | 38,000 | 80,257 |

As shown in Table 3, line AZ395, which contains the mutant allele ACSDMR001, has high resistance to the downy mildew pathogen *Peronospora farinosa* f. sp. *beticola* showing no evidence of infection. The use of this line in the development of new varieties will help limit the effects of the disease on future crops.

Example 22

Comparison of Inbred Beet AZ395 and Hybrid Beets BEH140 and BEH143 Versus Commercial Varieties As shown in Table 4, inbred line AZ395 and hybrid beets BEH140 and BEH143, which contain the mutant allele of the present invention, were evaluated for their quantifiable resistance to Pfb infection and compared to the commercial beet varieties Red Ace, Kestrel, Detroit Short Top, Detroit Supreme, and Ruby Queen, as well as the chard variety Gazelle, a rhubarb variety and the Pfb susceptible check A97601. Seedlings were inoculated with 70,000 spores/mL and then all plants in the flat were harvested into a plastic bag. All of the seedlings from the flat were weighed prior to adding 100 mL water. Seedlings were shaken for 1 minute in a 0.5 gallon plastic bag with the 100 mL of water. After shaking vigorously, liquid was poured through 4 layers of cheese cloth into a flask. Approximately one drop was dispensed on the counting chamber, and spores were counted under a compound microscope and the number recorded in spores/mL of liquid. Table 4 shows the variety name in column 1, the plant weight (g) in column 2, the bag weight (g) in column 3, the water added (mL) in column 4, the sporangia concentration (sp/mL) in column 5, and the sporangia per leaf tissue (sp/g) in column 6.

TABLE 4

| Variety | Plant weight (g) | Bag weight (g) | Water (mL) | Sporangia (sp/mL) | Sporangia/ Leaf tissue (sp/g) |
| --- | --- | --- | --- | --- | --- |
| AZ395 | 41.19 | 4.72 | 100 | 0 | 0 |
| BEH140 | 47.87 | 4.5 | 100 | 555.5 | 1,280.8 |
| BEH143 | 59.3 | 4.6 | 100 | 555.5 | 1,015.5 |
| A97601 | 32.6 | 4.61 | 100 | 40,000 | 142,908.2 |
| Gazelle | 31.22 | 4.6 | 100 | 4,500 | 16,904.6 |
| Red Ace | 26.1 | 4.57 | 100 | 13,000 | 60,380.9 |
| Kestrel | 35.82 | 4.55 | 100 | 8,000 | 25,583.6 |
| Detroit Short Top | 11.73 | 4.6 | 100 | 4,500 | 63,113.6 |
| Detroit Supreme | 35.2 | 4.6 | 100 | 6,250 | 20,424.8 |
| Ruby Queen | 39.79 | 4.57 | 100 | 28,000 | 79,500.3 |
| Rhubarb | 33.94 | 4.6 | 100 | 22,000 | 74,983.0 |

As shown in Table 4, inbred line AZ395 and hybrid lines BEH140 and BEH143, all of which contain the mutant allele of the present invention, have high resistance to the downy mildew pathogen *Peronospora farinosa* f. sp. *beticola* and have little to no evidence of infection, as shown in column 6 of Table 4.

Example 23

Randomized Complete Block Design Comparing Inbred Line AZ395 and Hybrid Lines BEH140 and BEH143 with Commercial Varieties As shown in Table 5, an experiment was set up as a Randomized Complete Block Design with four replications in which inbred line AZ395 and hybrid beet lines BEH140 and BEH143 were evaluated for their quantifiable resistance to Pfb infection and compared to the commercial beet varieties Red Ace, Kestrel, Detroit Short Top, Detroit Supreme, and Ruby Queen, as well as the chard variety Gazelle, a rhubarb variety and the Pfb susceptible check A97601. Each replication was comprised of a single row for each of the 11 entries. There were a total of four rows of plants for each entry randomized within each replication. Seedlings were inoculated twice, once with 21,000 spores/mL and a second time with 12,000 spores/mL. The data in Table 5 summarizes all four replications for each of the entries. Table 5 shows the variety name in column 1, plant weight (g) in column 2, container weight (g) in column 3, water added (mL) in column 4, sporangia concentration (sp/mL) in column 5, and the sporangia per leaf tissue (sp/g) in column 6.

TABLE 5

| Variety | Plant weight (g) | Container weight (g) | Water (mL) | Sporangia (sp/mL) | Sporangia/ Leaf tissue (sp/g) |
| --- | --- | --- | --- | --- | --- |
| AZ395 | 31.13 | 22.99 | 50 | 0.0 | 0.0 |
| BEH140 | 33.89 | 23.04 | 50 | 0.0 | 0.0 |
| BEH143 | 34.23 | 23.01 | 50 | 125.0 | 499.6 |
| A97601 | 26.27 | 23.0 | 50 | 2,902.8 | 40,467.0 |
| Gazelle | 30.33 | 22.93 | 50 | 1,562.5 | 12,234.0 |
| Red Ace | 28.15 | 22.95 | 50 | 2,430.5 | 23,915.0 |
| Kestrel | 31.33 | 22.84 | 50 | 3,872.0 | 26,968.0 |
| Detroit Short Top | 24.69 | 23.08 | 50 | 1,909.8 | 71,691.0 |
| Detroit Supreme | 27.26 | 23.01 | 50 | 3,090.3 | 37,281.0 |
| Ruby Queen | 28.63 | 22.98 | 50 | 3,889.0 | 34,291.0 |
| Rhubarb | 27.6 | 23.27 | 50 | 4,027.5 | 54,753.0 |

As shown in Table 5, inbred line AZ395 and hybrid lines BEH140 and BEH143, all of which contain the mutant allele of the present invention, have high resistance to the downy mildew pathogen *Peronospora farinosa* f. sp. *beticola* and have little to no evidence of infection, as shown in column 6 of Table 5.

Example 24

Identification of a Marker for the Mutant Allele of the Present Invention

A marker for the mutant allele of the present invention is identified using standard protocols. The identified marker is used to assess beet plants for the allele of the present invention and to aid in breeding new beet plants.

Further Embodiments of the Invention

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed and the present invention, in particular embodiments, also relates to transformed versions of the claimed variety or line.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed beet plants using transformation methods as described below to incorporate transgenes into the genetic material of the beet plant(s).

Expression Vectors for Beet Transformation: Marker Genes

Expression vectors include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., *Proc. Natl. Acad. Sci. USA*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford et al., *Plant Physiol.* 86:1216 (1988), Jones et al., *Mol. Gen. Genet.*, 210:86 (1987), Svab et al., *Plant Mol. Biol.* 14:197 (1990), Hille et al., *Plant Mol. Biol.* 7:171 (1986)). Other selectable marker genes confer resistance to herbicides such as glyphosate, glufosinate or bromoxynil (Comai et al., *Nature* 317:741-744 (1985), Gordon-Kamm et al., *Plant Cell* 2:603-618 (1990) and Stalker et al., *Science* 242:419-423 (1988)).

Selectable marker genes for plant transformation not of bacterial origin include, for example, mouse dihydrofolate reductase, plant 5-enolpyruvylshikimate-3-phosphate synthase and plant acetolactate synthase (Eichholtz et al., *Somatic Cell Mol. Genet.* 13:67 (1987), Shah et al., *Science* 233:478 (1986), Charest et al., *Plant Cell Rep.* 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase (Jefferson, R. A., *Plant Mol. Biol. Rep.* 5:387 (1987), Teeri et al., *EMBO J.* 8:343 (1989), Koncz et al., *Proc. Natl. Acad. Sci. USA* 84:131 (1987), DeBlock et al., *EMBO J.* 3:1681 (1984)).

In vivo methods for visualizing GUS activity that do not require destruction of plant tissue are available (Molecular Probes publication 2908, IMAGENE GREEN, pp. 1-4 (1993) and Naleway et al., *J. Cell Biol.* 115:151a (1991)). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells (Chalfie et al., *Science* 263: 802 (1994)). GFP and mutants of GFP may be used as screenable markers.

Expression Vectors for Beet Transformation: Promoters

Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters that initiate transcription only in a certain tissue are referred to as "tissue-specific". A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters—An inducible promoter is operably linked to a gene for expression in beet. Optionally, the inducible promoter is operably linked to a nucleotide sequence encoding a signal sequence which is operably linked to a gene for expression in beet. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Mett et al., *Proc. Natl. Acad. Sci. USA* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38

(1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. USA* 88:0421 (1991)).

B. Constitutive Promoters—A constitutive promoter is operably linked to a gene for expression in beet or the constitutive promoter is operably linked to a nucleotide sequence encoding a signal sequence which is operably linked to a gene for expression in beet.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2: 163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)). The ALS promoter, Xbal/Ncol fragment 5' to the *Brassica napus* ALS3 structural gene (or a nucleotide sequence similarity to said Xbal/Ncol fragment), represents a particularly useful constitutive promoter. See PCT application WO 96/30530.

C. Tissue-specific or Tissue-preferred Promoters—A tissue-specific promoter is operably linked to a gene for expression in beet. Optionally, the tissue-specific promoter is operably linked to a nucleotide sequence encoding a signal sequence which is operably linked to a gene for expression in beet. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai et al., *Science* 23:476-482 (1983) and Sengupta-Gopalan et al., *Proc. Natl. Acad. Sci. USA* 82:3320-3324 (1985)); a leaf-specific and light-induced promoter such as that from cab or rubisco (Simpson et al., *EMBO J.* 4(11): 2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., *Plant Mol. Biol.* 20:49 (1992); Close, P. S., Master's Thesis, Iowa State University (1993); Knox, C., et al., *Plant Mol. Biol.* 9:3-17 (1987); Lerner et al., *Plant Physiol.* 91:124-129 (1989); Frontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is a beet plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. *tomato* encodes a protein kinase); Mindrinos et al. *Cell* 78:1089 (1994) (*Arabidopsis* RSP2 gene for resistance to *Pseudomonas syringae*).

B. A gene conferring resistance to a pest, such as soybean cyst nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US 93/06487 which teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., which discloses genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

L. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M. A hydrophobic moment peptide. See PCT application WO 95/16776, which discloses peptide derivatives of tachyplesin which inhibit fungal plant pathogens, and PCT application WO 95/18855 which teaches synthetic antimicrobial peptides that confer disease resistance.

N. A membrane permease, a channel former or a channel blocker. For example, see the disclosure of Jaynes et al., *Plant Sci* 89:43 (1993), of heterologous expression of a cecropin-β lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus and tobacco mosaic virus.

P. An insect-specific antibody or an immunotoxin derived therefrom. Thus, an antibody targeted to a critical metabolic function in the insect gut would inactivate an affected enzyme, killing the insect. See Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

S. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S., *Current Biology*, 5(2) (1995).

U. Antifungal genes. See Cornelissen and Melchers, *Plant Physiol.*, 101:709-712 (1993); Parijs et al., *Planta* 183:258-264 (1991) and Bushnell et al., *Can. J. of Plant Path.* 20(2): 137-149 (1998).

V. Genes that confer resistance to *Phytophthora* root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif. (1995).

2. Genes That Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall et al., *Theor. Appl. Genet.* 83:435 (1992).

C. An herbicide that inhibits photosynthesis, such as a triazine (psbA and gs+ genes) and a benzonitrile (nitrilase gene). Przibila et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441 and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., *Plant Physiol.,* 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes That Confer or Contribute to a Value-Added Trait, such as:

A. Modified fatty acid metabolism, for example, by transforming a plant with an antisense gene of stearyl-ACP desaturase to increase stearic acid content of the plant. See Knultzon et al., *Proc. Natl. Acad. Sci. USA* 89:2625 (1992).

B. Decreased phytate content—1) Introduction of a phytase-encoding gene enhances breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. This could be accomplished by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteriol.* 170:810 (1988) (nucleotide sequence of *Streptococcus mutants* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus licheniformis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

D. Elevated oleic acid via FAD-2 gene modification and/or decreased linolenic acid via FAD-3 gene modification. See U.S. Pat. Nos. 6,063,947; 6,323,392; and international publication WO 93/11245.

4. Genes that Control Male Sterility:

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., *Plant Mol. Biol.* 19:611-622, 1992).

Methods for Beet Transformation

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc. Boca Raton, 1993) pp. 67-88. In addition, expression vectors and in-vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pp. 89-119.

A. *Agrobacterium*-Mediated Transformation

One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra and Moloney et al., *Plant Cell Reports* 8:238 (1989). See also, U.S. Pat. No. 5,563,055 (Townsend and Thomas), issued Oct. 8, 1996.

B. Direct Gene Transfer

Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987); Sanford, J. C., *Trends Biotech.* 6:299 (1988); Klein et al., *Bio/Tech.* 6:559-563 (1988); Sanford, J. C. *Physiol Plant* 7:206 (1990); Klein et al., *Biotechnology* 10:268 (1992). See also U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.*, 4:2731 (1985); Christou et al., *Proc Natl. Acad. Sci. USA* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described (Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994)).

Following transformation of beet target tissues, expression of the above-described selectable marker genes allows for preferential selection of transformed cells, tissues and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular beet line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple X by Y cross or the process of backcrossing depending on the context.

Gene Conversions

When the term "beet plant" is used in the context of the present invention, this also includes any single gene conversions of that variety. The term gene converted plant as used herein refers to those beet plants which are developed by a plant breeding technique called backcrossing wherein essentially all of the desired morphological and physiological characteristics of a variety are recovered in addition to the one or more genes transferred into the variety via the backcrossing technique. Backcrossing methods can be used with the present invention to improve or introduce at least one characteristic into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental beet plant that contributes the one or more genes for the desired characteristics is termed the nonrecurrent or donor parent. This terminology refers to the fact that the nonrecurrent parent is used one time in the backcross protocol and therefore does not recur. The parental beet plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the gene(s) of interest to be transferred. The resulting progeny from this cross are then crossed again to the recurrent parent and the process is repeated until a beet plant is obtained wherein essentially all of the desired morphological and physiological characteristics of the recurrent parent are recovered in the converted plant, in addition to the transferred gene(s) from the nonrecurrent parent.

The selection of a suitable recurrent parent is an important step for a successful backcrossing procedure. The goal of a backcross protocol is to alter or substitute one or more traits or characteristics in the original variety. To accomplish this, at least one gene of the recurrent variety is modified or substituted with the desired gene(s) from the nonrecurrent parent, while retaining essentially all of the rest of the desired genetic, and therefore the desired physiological and morphological, constitution of the original variety. The choice of the particular nonrecurrent parent will depend on the purpose of the backcross; one of the major purposes is to add some agronomically important trait to the plant. The exact backcrossing protocol will depend on the characteristic(s) or trait(s) being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic(s) has/have been successfully transferred.

Many traits have been identified that are not regularly selected for in the development of a new variety but that can be improved by backcrossing techniques. These traits may or may not be transgenic; examples of these traits include but are not limited to, male sterility, herbicide resistance, resistance for bacterial, fungal, or viral disease, insect resistance, male fertility, enhanced nutritional quality, industrial usage, yield stability and yield enhancement. These genes are generally inherited through the nucleus. Several of these traits are described in U.S. Pat. Nos. 5,959,185; 5,973,234 and 5,977,445; the disclosures of which are specifically hereby incorporated by reference for this purpose.

Tissue Culture

Further reproduction of a variety can occur by tissue culture and regeneration. Tissue culture of various tissues of beet and regeneration of plants therefrom is well known and widely published. For example, reference may be had to Jelaska, S. et al., *Physiol. Plant.* 64(2):237-242 (1985) and Krsnik-Rasol, M., *Int. J. Dev. Biol.* 35(3):259-263 (1991). Thus, another aspect of this invention is to provide cells which upon growth and differentiation produce beet plants having the mutant allele ACSDMR001.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

A deposit of the Alf Christianson Seed Company proprietary beet seed containing mutant allele ACSDMR001 of the present invention disclosed above and recited in the appended claims has been made with the American Type Culture Collection (ATCC), 10801 University Boulevard, Manassas, Va. 20110. The date of deposit was Feb. 7, 2012. The deposit of 2,500 seeds was taken from the same deposit maintained by Alf Christianson Seed Company since prior to the filing date of this application. All restrictions will be irrevocably removed upon granting of a patent, and the deposit is intended to meet all of the requirements of 37 C.F.R. §§1.801-1.809. The ATCC Accession Number is PTA-12501. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

What is claimed is:

1. A beet plant having a high resistance level to downy mildew, wherein said high resistance is conferred by mutant allele ACSDMR001, wherein a representative sample of seed containing said allele ACSDMR001 was deposited under ATCC Accession No. PTA-12501.

2. A beet plant, or a part thereof, produced by growing a beet seed containing a mutant allele designated ACSDMR001, wherein a representative sample of seed containing said allele ACSDMR001 was deposited under ATCC Accession No. PTA-12501.

3. A tissue culture of cells produced from the beet plant of claim 2, wherein said cells of tissue culture are produced from a plant part selected from the group consisting of embryos, meristematic cells, callus, pollen, leaves, anthers, stems, petioles, roots, root tips, fruits, seeds, flowers, cotyledons, and hypocotyls.

4. A protoplast produced from the tissue culture of claim 3.

5. A beet plant regenerated from the tissue culture of claim 3, wherein said beet plant exhibits a high resistance level to downy mildew.

6. A method for producing a beet seed, wherein the method comprises crossing the plant of claim 2 with a different beet plant and harvesting the resultant beet seed.

7. A beet seed produced by the method of claim 6.

8. A beet plant, or a part thereof, produced by growing said seed of claim 7.

9. A method of producing an herbicide resistant beet plant, wherein the method comprises transforming the beet plant of claim 2 with a transgene, wherein the transgene confers resistance to an herbicide selected from the group consisting of imidazolinone, sulfonylurea, glyphosate, glufosinate, L-phosphinothricin, triazine and benzonitrile.

10. An herbicide resistant beet plant produced by the method of claim 9.

11. A method of producing an insect resistant beet plant, wherein the method comprises transforming the beet plant of claim 2 with a transgene that confers insect resistance.

12. An insect resistant beet plant produced by the method of claim 11.

13. The beet plant of claim 12, wherein the transgene encodes a *Bacillus thuringiensis* endotoxin.

14. A method of producing a disease resistant beet plant, wherein the method comprises transforming the beet plant of claim 2 with a transgene that confers disease resistance.

15. A disease resistant beet plant produced by the method of claim 14.

16. A method of producing a beet plant with modified fatty acid metabolism or modified carbohydrate metabolism, wherein the method comprises transforming the beet plant of claim 2 with a transgene encoding a protein selected from the group consisting of fructosyltransferase, levansucrase, α-amylase, invertase and starch branching enzyme or DNA encoding an antisense of stearyl-ACP desaturase.

17. A beet plant having modified fatty acid metabolism or modified carbohydrate metabolism produced by the method of claim 16.

18. The beet plant of claim 2, wherein the plant has a high resistance level to downy mildew, and wherein said high resistance level to downy mildew is conferred by mutant allele ACSDMR001.

19. The beet plant of claim 18, wherein the plant has a high resistance level to downy mildew and exhibits a decreased average number of downy mildew sporangia per grams of leaf tissue, wherein said high resistance level is exhibiting at least 75% less average number of downy mildew sporangia per grams of leaf tissue per plant when compared to commercial beet varieties in an environment having a level of downy mildew present.

20. The beet plant of claim 18, wherein the plant has a high resistance level to downy mildew and exhibits a decreased average number of downy mildew sporangia per grams of leaf tissue, wherein said high resistance level is exhibiting at least 50% less average number of downy mildew sporangia per grams of leaf tissue per plant when compared to commercial beet varieties in an environment having a level of downy mildew present.

21. The beet plant of claim 18, wherein the plant has a high resistance level to downy mildew and exhibits a decreased average number of downy mildew sporangia per grams of leaf tissue, wherein said high resistance level is exhibiting at least 25% less average number of downy mildew sporangia per grams of leaf tissue per plant when compared to commercial beet varieties in an environment having a level of downy mildew present.

22. A method for producing an $F_1$ beet seed, wherein the method comprises crossing the plant of claim 18 with a different beet plant and harvesting the resultant $F_1$ hybrid beet seed.

23. A hybrid beet plant exhibiting increased resistance to downy mildew, or a part thereof, produced by growing said hybrid seed of claim 22.

* * * * *